US009873746B2

(12) United States Patent
Cregg et al.

(10) Patent No.: US 9,873,746 B2
(45) Date of Patent: Jan. 23, 2018

(54) METHODS OF SYNTHESIZING HETEROMULTIMERIC POLYPEPTIDES IN YEAST USING A HAPLOID MATING STRATEGY

(75) Inventors: James M. Cregg, Claremont, CA (US); John Latham, Seattle, WA (US); Mark Litton, Seattle, WA (US); Randall Schatzman, Redmond, WA (US); Ilya Tolstrorukov, Claremont, CA (US)

(73) Assignees: KECK GRADUATE INSTITUTE, Claremont, CA (US); ALDERBIO HOLDINGS LLC, Las Vegas, NV (US)

( * ) Notice: Subject to any disclaimer, the term of this patent is extended or adjusted under 35 U.S.C. 154(b) by 212 days.

(21) Appl. No.: 13/070,583

(22) Filed: Mar. 24, 2011

(65) Prior Publication Data
US 2011/0183402 A1 Jul. 28, 2011

Related U.S. Application Data

(63) Continuation of application No. 11/429,053, filed on May 8, 2006, now Pat. No. 7,927,863, which is a continuation-in-part of application No. 10/577,074, filed as application No. PCT/US2004/035302 on Oct. 22, 2004, now Pat. No. 8,268,582.

(60) Provisional application No. 60/513,876, filed on Oct. 22, 2003.

(51) Int. Cl.
| | |
|---|---|
| *C12N 15/81* | (2006.01) |
| *C07K 16/28* | (2006.01) |
| *C07K 16/00* | (2006.01) |
| *C07K 16/18* | (2006.01) |

(52) U.S. Cl.
CPC .......... *C07K 16/2896* (2013.01); *C07K 16/00* (2013.01); *C07K 16/18* (2013.01); *C07K 16/2809* (2013.01); *C12N 15/81* (2013.01); *C12N 15/815* (2013.01); *C07K 2317/24* (2013.01)

(58) Field of Classification Search
None
See application file for complete search history.

(56) References Cited

U.S. PATENT DOCUMENTS

| | | | | |
|---|---|---|---|---|
| 4,775,622 A | | 10/1988 | Hitzeman et al. | |
| 5,324,660 A | * | 6/1994 | Gleeson ................. | C07K 14/65 435/254.23 |
| 5,844,089 A | | 12/1998 | Hoffman et al. | |
| 6,204,023 B1 | * | 3/2001 | Robinson ................ | C12N 9/88 424/133.1 |
| 6,258,559 B1 | | 7/2001 | Zamost | |
| 6,306,625 B1 | | 10/2001 | Jacobs et al. | |
| 2003/0186374 A1 | * | 10/2003 | Hufton ............... | C12N 15/1037 506/1 |
| 2006/0121565 A1 | * | 6/2006 | Jonson ................... | C07K 14/58 435/69.1 |

FOREIGN PATENT DOCUMENTS

| | | |
|---|---|---|
| JP | H04339259 | 11/1992 |
| JP | 2000502901 | 3/2000 |
| JP | 3691055 | 8/2005 |
| WO | WO 91/02057 | 2/1991 |
| WO | WO 94/18330 | 8/1994 |
| WO | WO 97/24445 | 7/1997 |
| WO | 00/23579 | 4/2000 |
| WO | WO 03/016525 | 2/2003 |
| WO | 03/018761 | 3/2003 |
| WO | 03/029456 | 4/2003 |

OTHER PUBLICATIONS

Cereghino et al in (Current Opinion in Biotechnology 2002, vol. 13, pp. 329-332).*
Cereghino & Cregg (FEMS Microbiology Reviews 2000, vol. 24, pp. 45-66).*
Blaise et al. Construction and Diversification of Yeast Cell Surface Displayed Libraries by Yeast Mating: Application to the Affinity Maturation of Fab Antibody Fragments, Gene, vol. 342, Sep. 2004, pp. 211-218.
Macauley-Patrick et al. Heterologous Protein Production Using the Pichia Pastoris Expression System, Yeast 22,(2005), pp. 249-270.
Kato S, et al. "Efficient expression, purification and characterization of mouse salivary alpha-amylase secreted from methylotrophic yeast, Pichia pastoris," Yeast. May 2001;18(7):643-55.
Murasugi A, et al. "Production of recombinant human bile salt-stimulated lipase in Pichia pastoris," Protein Expr Purif. Nov. 2001;23(2):282-8.
Wang Y, et al. "Production of an anti-prostate-specific antigen single-chain antibody fragment from Pichia pastoris," Protein Expr Purif. Dec. 2001;23(3):419-25.
Murasugi A, et al. "Comparison of three signals for secretory expression of recombinant human midkine in Pichia pastoris," Biosci Biotechnol Biochem. Oct. 2001;65(10):2291-3.
Chen, M. et al., "Generation of diploid Pichia pastoris strains by mating and their application for recombinant protein production", Microbial Cell Factories, 2012, 11:91, 1-18.
Crandall M, et al. "Induction of haploid glycoprotein mating factors in diploid yeasts," Methods Cell Biol. 1975;12:185-207.
NCBI Taxonomy Browser (online), Taxonomy ID:4907 [analyzed @ Oct. 7, 2011] url:http://www.ncbi.nlm.nih.gov/Taxonomy/Browser/wwwtax.cgi?id=4907 ( 1 page).

* cited by examiner

*Primary Examiner* — Catherine S Hibbert
(74) *Attorney, Agent, or Firm* — Robin L. Teskin; LeClairRyan A Professional Corporation

(57) ABSTRACT

Methods are provided for the synthesis and secretion of recombinant proteins preferably large mammalian proteins or hetero-multimeric proteins at high levels and for prolonged time in polyploid, preferably diploid yeast. These methods use various mating competent yeast, including *Pichia*. In a preferred embodiment, a first expression vector is transformed into a first haploid cell; and a second expression vector is transformed into a second haploid cell. The transformed haploid cells, each individually synthesizing a non-identical polypeptide, are identified and then genetically crossed or fused. The resulting diploid strains are utilized to produce and secrete fully assembled and biologically functional hetero-multimeric protein.

8 Claims, 4 Drawing Sheets

US 9,873,746 B2

METHODS OF SYNTHESIZING HETEROMULTIMERIC POLYPEPTIDES IN YEAST USING A HAPLOID MATING STRATEGY

RELATED APPLICATIONS

This application is a continuation of U.S. Ser. No. 11/429,053 filed May 8, 2006, which is a continuation-in-part of U.S. Ser. No. 10/577,074 with a 371 filing date of May 7, 2007, which is the US national phase of PCT/US04/35302 filed on Oct. 22, 2004, which in turn claims benefit of priority to provisional patent application U.S. Ser. No. 60/513,876 filed on Oct. 22, 2003. All of these patent applications are expressly incorporated by reference in their entireties herein.

BACKGROUND OF THE INVENTION

Recombinant protein production is an essential activity for high throughput screening, functional validation, structural biology, and production of pharmaceutical polypeptides. *Escherichia coli* is a widely used organism for the expression of heterologous proteins because it easily grows to a high cell density on inexpensive substrates, and has well-established genetic techniques and expression vectors. However, this is not always sufficient for the efficient production of active biomolecules. In order to be biologically active, polypeptide chains have to fold into the correct native three-dimensional structure, including the appropriate formation of disulfide bonds, and may further require correct association of multiple chains.

Although the active state of the protein may be thermodynamically favored, the time-scale for folding can vary from milliseconds to days. Kinetic barriers are introduced, for example, by the need for alignment of subunits and sub-domains. And particularly with eukaryotic proteins, covalent reactions must take place for the correctly folded protein to form. The latter types of reaction include disulfide bond formation, cis/trans isomerization of the polypeptide chain around proline peptide bonds, preprotein processing and the ligation of prosthetic groups. These kinetic limitations can result in the accumulation of partially folded intermediates that contain exposed hydrophobic 'sticky' surfaces that promote self-association and the formation of aggregates.

The expression of multimeric proteins such as hormones and enzymes in active form in particular is difficult to achieve in some recombinant expression systems. Many host cells do not possess the appropriate enzymes to process such proteins in biologically active form. Because of these difficulties such multimeric proteins usually must be expressed in mammalian cells. This unfortunately raises the costs associated with producing the protein as well as resulting in issues of viral contamination which are particularly problematic if the multimeric protein is to be used a therapeutic. One prevalent example of a multimeric protein typical produced in mammalian culture systems such as CHO cells is recombinant immunoglobulins or antibodies.

Antibodies are tetrameric proteins, which have many uses in clinical diagnosis and therapy. Each antibody tetramer is composed of two identical light chains and two identical heavy chains. Pure human or humanized antibodies of a specific type are difficult or impossible to purify in sufficient amounts for many purposes from natural sources. As a consequence, biotechnology and pharmaceutical companies have turned to recombinant DNA-based methods to prepare them on a large scale. The production of functional antibodies requires not just the synthesis of the two polypeptides but also a number of post-translational modifications, including proteolytic processing of the N-terminal secretion signal sequence; proper folding and assembly of the polypeptides into tetramers; formation of disulfide bonds; and specific N-linked glycosylation. All of these events take place in the eukaryotic cell secretory pathway, an organelle complex unique to eukaryotic cells.

Recombinant synthesis of such complex proteins has had to rely on higher eukaryotic tissue culture-based systems for biologically active material. However, as mentioned mammalian tissue culture based production systems are significantly more expensive and complicated than microbial fermentation methods. In addition, there continues to be questions regarding therapeutic products produced using materials derived from animal by-products.

Alternatives to mammalian expression systems for the expression of recombinant proteins are eukaryotic microbia such as yeast and insect cell expression systems. Insect cell expression systems use baculovirus vectors and often achieve high yields of secreted proteins. However, such cells are not always capable of processing complex mammalian polypeptides in active form. Yeast find fairly well established usage in expressing recombinant proteins. The most typically used yeast is *Saccharomyces* since it has been well characterized, many promoters suitable for use therein are widely available as are sequences for facilitating secretion such as the alpha and A factor secretory signal sequences. Another yeast which has been suggested to be capable of producing mammalian proteins in active form is *Pichia*, and particularly *Pichia pastoris*. As a eukaryote, *Pichia pastoris* has many of the advantages of higher eukaryotic expression systems such as protein processing, protein folding, and posttranslational modification, while being as easy to manipulate as *E. coli* or *Saccharomyces cerevisiae*. It is faster, easier, and less expensive to use than other eukaryotic expression systems such as baculovirus or mammalian tissue culture, and generally gives higher expression levels. As a yeast, it shares the advantages of molecular and genetic manipulations with *Saccharomyces*. These features make *Pichia* very useful as a protein expression system. In addition various other types of yeast have been disclosed to be suitable for expression of heterologous polypeptides.

Many of the techniques developed for *Saccharomyces* may be applied to *Pichia* as well as to other types of yeast. These include transformation by complementation; gene disruption and gene replacement. In addition, the genetic nomenclature used for *Saccharomyces* has been applied to *Pichia*. There is also cross-complementation between gene products in both *Saccharomyces* and *Pichia*. Several wild-type genes from *Saccharomyces* complement comparable mutant genes in *Pichia*.

Heterologous expression in *Pichia pastoris* as well as other types of yeast can be either intracellular or secreted. Secretion requires the presence of a signal sequence on the expressed protein to target it to the secretory pathway. While several different secretion signal sequences have been used successfully, including the native secretion signal present on some heterologous proteins, success has been variable. A potential advantage to secretion of heterologous proteins is that *Pichia pastoris* secretes very low levels of native proteins. That, combined with the very low amount of protein in the minimal *Pichia* growth medium, means that the secreted heterologous protein comprises the vast majority of the total protein in the medium and serves as the first step in purification of the protein.

Many species of yeast, including *Pichia*, are mating competent. This enables two distinct haploid strains to mate naturally and generate a diploid species possessing two chromosomal copies Alternatively, polyploid yeast can be obtained by artificial methods, i.e., spheroplast fusion.

As noted yeast including *Pichia* have been used many years for the production of heterologous proteins. Although *P. pastoris* in particular has been used successfully for the production of various heterologous proteins, e.g., hepatitis B surface antigen (Cregg et al. (1987) Bio/Technology 5:479), lysozyme and invertase (Digan et al. (1988) *Dev. Indust. Micro.* 29:59; Tschopp et al. (1987) *Bio/Technoloqy* 5:1305), endeavors to produce other heterologous gene products in *Pichia*, especially by secretion, have given mixed results. At the present level of understanding of the *P. pastoris* expression system, it is unpredictable whether a given gene can be expressed to an appreciable level in this yeast or whether *Pichia* will tolerate the presence of the recombinant gene product in its cells. Further, it is especially difficult to foresee if a particular protein will be secreted by *P. pastoris*, and if it is, at what efficiency.

Additionally, prior to the present invention the use of diploid yeast to secrete heterologous polypeptides had not been reported. Rather, the earlier work using yeast to produce secreted heterologous polypeptides was limited to haploidal yeast expression systems. In fact, earlier evidence suggested that diploid yeast such as *Pichia* would be incapable of stably expressing and secreting heterologous polypeptides in amounts required for such expression systems to be suitable for commercial use.

The present invention therefore provides improved methods and compositions of matter that provide for the secretion of heterologous polypeptides, preferably heteromultimers using polyploidal yeast cultures preferably produced from mating competent yeast, including *Pichia* and other genera.

OBJECTS OF THE INVENTION AND PREFERRED EMBODIMENTS

It is an object of the invention to provide polyploid yeast cultures which stably express and secrete into the culture medium at least one heterologous polypeptide in amounts of at least 10-25 mg/liter, more preferably at least 25-100 mg/liter, still more preferably 100-250 mg/liter, even more preferably 250-500 mg/liter, yet more preferably 500-1000 mg/liter and most preferably in excess of 1 g/liter. These cultures will preferably stably express the polypeptide at such levels for at least several days to a week, more preferably at least a month, still more preferably at least 1-6 months, and most preferably up to a year or longer It is another object of the invention to provide a method for producing a polyploid yeast culture that stably expresses and secretes into the culture medium at least 10-25 mg/liter of at least one heterologous polypeptide comprising: (i) introducing a first expression vector containing a heterologous DNA that encodes a first desired polypeptide operably linked to a promoter and a signal sequence into a haploid cell; (ii) optionally introducing into a second haploid yeast cell a second expression vector that contains a heterologous DNA which encodes a second heterologous polypeptide also operably linked to a promoter and a signal sequence (iii) producing by mating or spheroplast fusion a polyploid yeast from said first and/or second haploid yeast cells; (iv) selecting polyploid yeast cells that express and secrete said first and/or second polypeptide; and (v) deriving polyploid yeast cultures therefrom that stably or for prolonged periods express in secreted form at least 10-25 mg/liter of said first and/or second polypeptide. In preferred embodiments the amount of secreted polypeptide will range from at least 25-100 mg/liter, more preferably 100-500 mg/liter, still more preferably 500-1000 mg/liter or more.

It is another preferred embodiment of the invention to provide a method for producing a diploid yeast that stable expresses at least 10-25 mg/liter of at least one desired heterologous polypeptide comprising: (i) introducing into a diploid yeast at least one desired heterologous polypeptide; (ii) selecting diploid yeast cells which stable express said at least one heterologous polypeptide; and (iii) generating a diploid culture therefrom that stably or for prolonged periods secretes at least 10-25 mg/liter of said at least one heterologous polypeptide. More preferably the yeast culture will express at least 25-50 mg/liter, still more preferably at least 50-250 mg/liter, even more preferably at least 250-500 mg/liter and most preferably at least 500-1000 mg/liter or more.

SUMMARY OF THE INVENTION

Methods are provided for the synthesis and secretion of recombinant polypeptides in polyploid yeast cells, preferably diploid *Pichia* yeast or other mating competent yeast cells. Most typically such recombinant proteins will comprise mammalian polypeptides which are to be used therapeutically such as recombinant enzymes, hormones, growth factors, cytokines or lymphokines, cytotoxins or lymphotoxins, immunoglobulins, tumor antigens, receptors, and the like. More preferably such proteins will comprise large mammalian proteins, i.e., at least proteins which are at least several hundred amino acids or even in excess of 1000 amino acids and will possess one or more cysteine residues and/or are glycosylated when expressed endogenously. Examples of such proteins include lymphokines, enzymes, growth factors, lymphokines or cytokines, tumor antigens, viral antigens, immunotoxins and cytotoxins, and the like. In an especially preferred embodiment the yeast expressed protein will be suitable for human therapy.

In a more preferred embodiment, the invention expresses secreted homo-polymeric or hetero-multimeric proteins in diploid yeast, preferably mating competent yeast, more preferably *Pichia*. Hetero-multimeric proteins of interest comprise at least two non-identical polypeptide chains, e.g. antibody heavy and light chains, MHC alpha and beta chains; heteropolymeric hormones, receptor polypeptides, and the like. For example such heteropolymeric proteins may comprise heteropolymeric G protein coupled receptors.

In practicing this embodiment of the invention expression vectors are preferably provided for the expression of each non-identical polypeptide chain. Alternatively, nucleic acid sequences encoding the non-identical polypeptide chains may be comprised on the same expression vector. Such expression vectors may be extrachromosomal or may be integrated into the diploid yeast cell's chromosomal DNA.

In the preferred embodiment a different expression vector is introduced into two different haploid yeast cells. Alternatively, an expression vector encoding one or more heterologous polypeptides, preferably those which associate to produce a heteropolymeric polypeptide having a desired functionality may be introduced into a single haploid yeast cell which is then mated or fused with another yeast cell to produce a diploid or polyploidal yeast cell. Still alternatively a vector or vectors encoding providing for the secretion of the desired polypeptide chains may be introduced into a haploid yeast cell and this cell fused or mated with another haploid cell to produce a diploid or tetraploid cell that expresses and secretes these polypeptides. Yet alternatively diploid yeast may be transformed with one or more vectors containing genes encoding and providing for the secretion of a desired heterologous polypeptide.

In some embodiments of the invention, the haploid yeast cell is genetically marked, where the haploid yeast cell is one of a complementary pair. A first expression vector is transformed into one haploid cell and a second expression vector is transformed into a second haploid cell. Where the haploid cells are to be mated this will be through direct genetic fusion, or a similar event is induced with spheroplast fusion.

The haploid yeast cells used for producing diploid or other polyploidal yeast cells expression may contain one or more genetic mutations which result in enhanced growth characteristics or enhanced secretory capacity or other improved phenotypic characteristic relative to yeast cells lacking the mutations. Yeast strains possessing such enhance characteristics are commercially available. Alternatively yeast cells may be mutagenized by known methods such as site specific mutagenesis or randomly using e.g., UV irradiation or the use of chemical mutagens and the resultant cultures screened to identify yeast strains possessing enhanced characteristics such as enhanced growth, stability, resistance to pathogens, or secretory capabilities relative to non-mutant strains.

The expression levels of the non-identical polypeptides in the haploid or diploid yeast cells may be individually calibrated, and adjusted through appropriate selection, vector copy number, promoter strength and/or induction and the like. In one embodiment of the invention, the promoter in each expression vector or on the same vector for expressing the different polypeptide subunits is different. Alternatively, if a polycistronic vector is used the positioning of the different genes on the construct may be varied (flipped) in order to favor the expression of one polypeptide relative to the other. In another embodiment of the invention, the same promoter is provided for the expression of each polypeptide. Promoters may be constitutive or inducible. The types of promoters that are useful in the invention include promoters from eukarotes such as yeast, insect, mammalian, viral, plant, fungal, amphibian, avian, and reptile sources. In general the promoters will comprise yeast, mammalian, or viral promoters. Most typically the promoters will be yeast promoters of highly expressed proteins.

In a preferred embodiment, the transformed haploid cells, each individually synthesizing a non-identical polypeptide, are identified and then genetically crossed or fused. The resulting diploid strains are utilized to produce and secrete fully assembled and biologically functional hetero-multimeric protein. The diploid methodology allows optimized subunit pairing to enhance full-length product generation and secretion.

However, as mentioned, the invention contemplates the expression and secretion of non-multimeric proteins in diploidal yeast cultures as well, especially large mammalian proteins, i.e., at least several hundred amino acids or even in excess of a thousand amino acids. As noted above, prior to the present invention experts in the field had believed that diploid yeast would be unsuitable for achieving stable and/or prolonged expression and secretion of recombinant polypeptides, especially large heterologous polypeptides in amounts sufficient to be commercially viable. By contrast the present inventors have surprisingly discovered that diploidal yeast cultures express and secrete into the culture medium for prolonged periods, i.e., from at least several days to at least a month or more, even for more than a year, amounts of recombinant polypeptide ranging from at least 10-25 mg/liter, 25-250 mg/liter, 250-500 mg/liter, 500-1000 mg/liter and even amounts in excess of 1 gram/liter. These results are truly unexpected.

BRIEF DESCRIPTION OF THE DRAWINGS

FIG. 1B shows selective detection of the H chain, which is found only in the parental H chain haploid, and mated diploid containing both H and L. FIG. 1C shows general detection of H & L chains, which establishes that protein production is active in all three strains. FIG. 1D shows selective detection in the diploid strain of correctly assembled full antibody, confirming that only the diploid system is capable of generating fully assembled antibody.

DETAILED DESCRIPTION OF THE INVENTION

Figure 1:
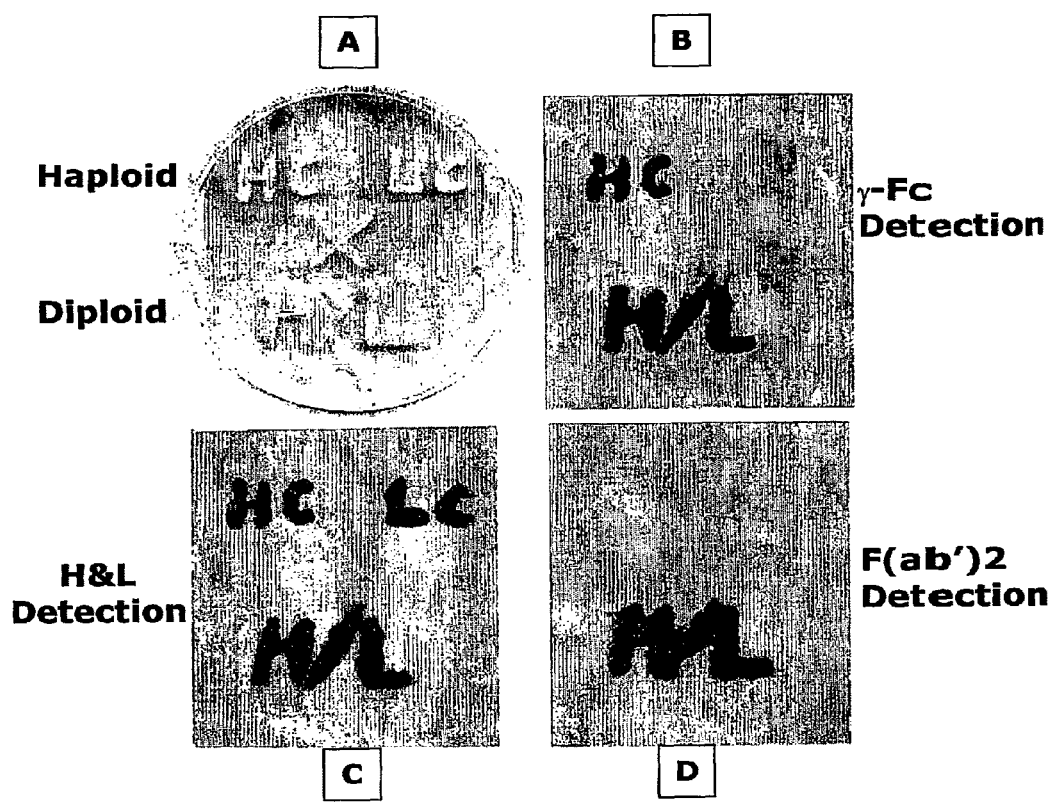
FIGS. 1A-1D. Generation of assembled full length recombinant antibody. Immunoblot detection methodology was used to characterize the parental haploid *Pichia* strains, each producing a subunit of the antibody and target diploid strain producing both subunits that form the fully assembled antibody. The yeast strains shown in FIG. 1A show a static culture of each of the representative strains, where the top portion is the distinct haploids strains containing Heavy (H) and Light (L) chain subunits respectively; the bottom the mated stable diploid producing both subunits.

Recombinant polypeptides, preferably large mammalian polypeptides or multimeric hetero-multimeric proteins are secreted from polyploidal, preferably diploid or tetraploid strains of mating competent yeast. The invention is directed to methods for producing recombinant polypeptides in secreted form for prolonged periods using cultures comprising polyploid yeast i.e. at least several days to a week, more preferably at least a month or several months, and even more preferably at least 6 months to a year or longer. These polyploid yeast cultures will express at least 10-25 mg/liter of the polypeptide, more preferably at least 50-250 mg/liter, still more preferably at least 500-1000 mg/liter, and most preferably a gram per liter or more of the recombinant polypeptide. The methods are especially useful for producing large mammalian proteins and multimeric polypeptides.

In one embodiment of the invention a pair of genetically marked yeast haploid cells are transformed with expression vectors comprising subunits of a desired heteromultimeric protein. One haploid cell comprises a first expression vector, and a second haploid cell comprises a second expression vector. In another embodiment diploid yeast cells will be transformed with one or more expression vectors that provide for the expression and secretion of one or more recombinant polypeptides. In still another embodiment a single haploid cell may be transformed with one or more vectors and used to produce a polyploidal yeast by fusion or mating strategies. In yet another embodiment a diploid yeast culture may be transformed with one or more vectors providing for the expression and secretion of a desired polypeptide or polypeptides. These vectors may comprise plasmids that are maintained extrachromosomally or may comprise vectors e.g., linearized plasmids that integrate into the yeast cell's genome randomly or by homologous recombination. Optionally, additional expression vectors may be introduced into the haploid or diploid cells; or the first or second expression vectors may comprise additional coding sequences; for the synthesis of heterotrimers; heterotetramers; etc. The expression levels of the non-identical polypeptides may be individually calibrated, and adjusted through appropriate selection, vector copy number, promoter strength and/or induction and the like. The transformed haploid cells are genetically crossed or fused. The resulting diploid or tetraploid strains are utilized to produce and secrete fully assembled and biologically functional proteins preferably hetero-multimeric proteins.

The use of diploid or tetraploid cells for protein production provides for unexpected benefits. The cells can be grown for production purposes, i.e. scaled up, and for extended periods of time, in conditions that can be deleterious to the growth of haploid cells, which conditions may include high cell density; growth in minimal media; growth at low temperatures; stable growth in the absence of selective pressure; and which may provide for maintenance of heterologous gene sequence integrity and maintenance of high level expression over time. Indeed the inventors have achieved expression yields in excess of about 1 g/liter and these yields may be enhanced by further optimization. Without wishing to be bound thereby, the inventors theorize that these benefits may arise, at least in part, from the creation of diploid strains from two distinct parental haploid strains. Such haploid strains can comprise numerous minor autotrophic mutations, which mutations are complemented in the diploid or tetraploid, enabling growth under highly selective conditions.

DEFINITIONS

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and the include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Mating Competent Yeast Species.

In the present invention this is intended to broadly encompass any diploid yeast which can be stably maintained in culture. Such species of yeast exist in a haploid and a diploid form. The diploid cells may, under appropriate conditions, proliferate for indefinite number of generations in the diploid form. Diploid cells can also sporulate to form haploid cells. In addition, sequential mating can result in tetraploid strains through further mating of the auxotrophic diploids. In the present invention the diploid or polyploidal yeast cells are preferably produced by mating or spheroplast fusion.

In one embodiment of the invention, the mating competent yeast is a member of the Saccharomycetaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis*; and *Zygosaccharomyces*. Other types of yeast potentially useful in the invention include *Yarrowia, Rhodosporidium, Candida, Hansenula, Filobasium, Filobasidellla, Sporidiobolus, Bullera, Leucosporidium* and *Filobasidella*.

The genus *Pichia* is of particular interest. *Pichia* comprises a number of species, including the species *Pichia pastoris, Pichia methanolica*, and *Hansenula polymorpha (Pichia angusta)*. Most preferred is the species *Pichia pastoris*.

Haploid Yeast Cell: A cell having a single copy of each gene of its normal genomic (chromosomal) complement.

Polyploid Yeast Cell A cell having more than one copy of its normal genomic (chromosomal) complement.

Diploid Yeast Cell: A cell having two copies (alleles) of every gene of its normal genomic complement, typically formed by the process of fusion (mating) of two haploid cells.

Tetraploid Yeast Cell. A cell having four copies (alleles) of every gene of its normal genomic complement, typically formed by the process of fusion (mating) of two haploid cells. Tetraploids may carry two, three, or four different cassettes. Such tetraploids might be obtained in *S. cerevisiae* by selective mating homozygotic heterothallic a/a and alpha/alpha diploids and in *Pichia* by sequential mating of haploids to obtain auxotrophic diploids. For example, a [met his] haploid can be mated with [ade his] haploid to obtain diploid [his]; and a [met arg] haploid can be mated with [ade arg] haploid to obtain diploid [arg]; then the diploid [his]× diploid [arg] to obtain a tetraploid prototroph. It will be understood by those of skill in the art that reference to the benefits and uses of diploid cells may also apply to tetraploid cells.

Yeast Mating: The process by which two haploid yeast cells naturally fuse to form one diploid yeast cell.

Meiosis: The process by which a diploid yeast cell undergoes reductive division to form four haploid spore products. Each spore may then germinate and form a haploid vegetatively growing cell line.

Selectable Marker: A selectable marker is a gene or gene fragment that confers a growth phenotype (physical growth characteristic) on a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two ts mutants are crossed or a ts mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to: ZEO; G418; HIS 5; LYS3; MET1; MET3a; ADE1; ADE3; URA3; and the like.

Expression Vector: These DNA species contain elements that facilitate manipulation for the expression of a foreign protein within the target host cell. Conveniently, manipulation of sequences and production of DNA for transformation is first performed in a bacterial host, e.g. E. coli, and usually vectors will include sequences to facilitate such manipulations, including a bacterial origin of replication and appropriate bacterial selection marker. Selectable markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media.

Expression vectors for use in the methods of the invention will further include yeast specific sequences, including a selectable auxotrophic or drug marker for identifying transformed yeast strains. A drug marker may further be used to amplify copy number of the vector in a yeast host cell.

The polypeptide coding sequence of interest is operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included, e.g. a signal sequence, and the like. A yeast origin of replication is optional, as expression vectors are often integrated into the yeast genome.

In one embodiment of the invention, the polypeptide of interest is operably linked, or fused, to sequences providing for optimized secretion of the polypeptide from yeast diploid cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites or alternatively via a PCR/recombination method familiar to those skilled in the art (Gateway® Technology; Invitrogen, Carlsbad Calif.). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequence to which they are operably linked. Such promoters fall into several classes: inducible, constitutive, and repressible promoters that increase levels of transcription in response to absence of a repressor. Inducible promoters may initiate increased levels of transcription from DNA under their control in response to some change in culture conditions, e.g., the presence or absence of a nutrient or a change in temperature.

The yeast promoter fragment may also serve as the site for homologous recombination and integration of the expression vector into the same site in the yeast genome; alternatively a selectable marker is used as the site for homologous recombination. *Pichia* transformation is described in Cregg et al. (1985) *Mol. Cell. Biol.* 5:3376-3385.

Examples of suitable promoters from *Pichia* include the AOX1 and promoter (Cregg et al. (1989) *Mol. Cell. Biol.* 9:1316-1323); ICL1 promoter (Menendez et al. (2003) *Yeast* 20(13):1097-108); glyceraldehyde-3-phosphate dehydrogenase promoter (GAP) (Waterham et al. (1997) *Gene* 186(1): 37-44); and FLD1 promoter (Shen et al. (1998) *Gene* 216(1):93-102). The GAP promoter is a strong constitutive promoter and the AOX and FLD1 promoters are inducible.

Other yeast promoters include GAPDH, ADH/GAP, alcohol dehydrogenase II, GAL4, PHO3, PHO5, Pyk, and chimeric promoters derived therefrom. Additionally, non-yeast promoters may be used in the invention such as mammalian, insect, plant, reptile, amphibian, viral, and avian promoters. Most typically the promoter will comprise a mammalian promoter (potentially endogenous to the expressed genes) or will comprise a yeast or viral promoter that provides for efficient transcription in yeast systems.

The polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell. The *S. cerevisiae* alpha factor pre-pro signal has proven effective in the secretion of a variety of recombinant proteins from *P. pastoris*. Other yeast signal sequences include the mating factor A signal sequence, the invertase signal sequence, and signal sequences derived from other secreted yeast polypeptides. Additionally, these signal peptide sequences may be engineered to provide for enhanced secretion in diploid yeast expression systems. Other secretion signals of interest also include mammalian signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g. K28 pre-protoxin sequence, PHA-E, FACE, human MCP-1, human serum albumin signal sequences, human Ig heavy chain, human Ig light chain, and the like. For example, see Hashimoto et. al. Protein Eng 11(2) 75 (1998); and Kobayashi et. al. Therapeutic Apheresis 2(4) 257 (1998).

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion and/or sequenced.

As an alternative to restriction and ligation of fragments, recombination methods based on att sites and recombination enzymes may be used to insert DNA sequences into a vector. Such methods are described, for example, by Landy (1989) Ann. Rev. Biochem. 58:913-949; and are known to those of skill in the art. Such methods utilize intermolecular DNA recombination that is mediated by a mixture of lambda and E. coli—encoded recombination proteins. Recombination occurs between specific attachment (att) sites on the interacting DNA molecules. For a description of att sites see Weisberg and Landy (1983) Site-Specific Recombination in Phage Lambda, in *Lambda II*, Weisberg, ed. (Cold Spring Harbor, N.Y.: Cold Spring Harbor Press), pp. 211-250. The DNA segments flanking the recombination sites are switched, such that after recombination, the att sites are hybrid sequences comprised of sequences donated by each parental vector. The recombination can occur between DNAs of any topology.

Alt sites may be introduced into a sequence of interest by ligating the sequence of interest into an appropriate vector; generating a PCR product containing aft B sites through the use of specific primers; generating a cDNA library cloned into an appropriate vector containing att sites; and the like.

Folding, as used herein, refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e. foldases, chaperonins, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic PDI is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of BIP (immunoglobulin heavy chain binding protein); cyclophilin; and the like. In one embodiment of the invention, each of the haploid parental strains expresses a distinct folding enzyme, e.g. one strain may express BIP, and the other strain may express PDI.

The terms "desired protein" or "target protein" are used interchangeably and refer generally to any secreted protein. Preferably this protein will comprise a large mamalian protein, typically at least 100 amino acids, more typically 100-500 amino acids or over a thousand amino acids long. In the exemplary embodiment, the desired protein will comprise a heteropolymeric protein comprised of 2 or more non-identical polypeptide chains, where such chains are independently synthesized, i.e. not resulting from post-translational cleavage of a single polypeptide chain. The polypeptides are heterologous, i.e., foreign, to the yeast. Preferably, mammalian polypeptides, i.e. polypeptides encoded in a mammalian genome are used. Examples of such proteins include hormones, growth factors, cytokines, lymphokines, enzymes, receptors, cytotoxins, lymphotoxin, immunotoxins, tumor polypeptides, viral polypeptides, antibodies et al. These proteins or the corresponding gene may be engineered to facilitate expression in diploid yeast, e.g., by removal of glycosylation sites, removal of one or more cysteine residues, use of yeast preferred codons, elimination of cleavage sites, and the like.

In a preferred embodiment, the protein is an antibody or a binding portion thereof. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Numerous antibody coding sequences have been described; and others may be raised by methods well-known in the art. Examples thereof include chimeric antibodies, human antibodies and other non-human mammalian antibodies, humanized antibodies, single chain antibodies (scFvs), camelbodies, SNIPS, and antibody fragments such as Fabs, Fab', Fab2 and the like.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions (VK and VH), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated fully herein by reference).

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), immunoglobulin fragments comprising the epitope binding site (e.g., Fab', F(ab')$_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a variable light chain region and a variable heavy chain region. Combinations of antibodies are also of interest, e.g. diabodies, which comprise two distinct Fv specificities.

Immunoglobulins may be modified post-translationally, e.g. to add chemical linkers, detectable moieties, such as fluorescent dyes, enzymes, substrates, chemiluminescent moieties and the like, or specific binding moieties, such as streptavidin, avidin, or biotin, and the like may be utilized in the methods and compositions of the present invention.

The term "polyploid yeast that stably expresses or expresses a desired secreted heterologous polypeptide for prolonged time" refers to a yeast culture that secretes said polypeptide for at least several days to a week, more preferably at least a month, still more preferably at least 1-6 months, and even more preferably for more than a year at threshold expression levels, typically at least 10-25 mg/liter and preferably substantially greater.

The term "polyploidal yeast culture that secretes desired amounts of recombinant polypeptide" refers to cultures that stably or for prolonged periods secrete at least 10-25 mg/liter of heterologous polypeptide, more preferably at least 50-500 mg/liter, and most preferably 500-1000 mg/liter or more.

Methods of Polypeptide Synthesis

Transformed mating competent haploid yeast cells provide a genetic method that enables subunit pairing of a desired protein. Haploid yeast strains are transformed with each of two expression vectors, a first vector to direct the synthesis of one polypeptide chain and a second vector to direct the synthesis of a second, non-identical polypeptide chain. The two haploid strains are mated to provide a diploid host where optimized target protein production can be obtained.

Optionally, additional non-identical coding sequence(s) are provided. Such sequences may be present on additional expression vectors or in the first or the second expression vectors. As is known in the art, multiple coding sequences may be independently expressed from individual promoters; or may be coordinately expressed through the inclusion of an "internal ribosome entry site" or "IRES", which is an element that promotes direct internal ribosome entry to the initiation codon, such as ATG, of a cistron (a protein encoding region), thereby leading to the cap-independent translation of the gene. IRES elements functional in yeast are described by Thompson et al. (2001) P.N.A.S. 98:12866-12868.

In one embodiment of the invention, antibody sequences are produced in combination with a secretary J chain, which provides for enhanced stability of IgA (see U.S. Pat. Nos. 5,959,177; and 5,202,422).

In a preferred embodiment the two haploid yeast strains are each auxotrophic, and require supplementation of media for growth of the haploid cells. The pair of auxotrophs are complementary, such that the diploid product will grow in the absence of the supplements required for the haploid cells. Many such genetic markers are known in yeast, including requirements for amino acids (e.g. met, lys, his, arg, etc.), nucleosides (e.g. ura3, ade1, etc.); and the like.

Amino acid markers may be preferred for the methods of the invention. Alternatively diploid cells which contain the desired vectors can be selected by other means, e.g., by use of other selectable markers, such as green fluorescent protein, various dominant selectable markers, and the like.

The two transformed haploid cells may be genetically crossed and diploid strains arising from this mating event selected by their hybrid nutritional requirements. Alternatively, populations of the two transformed haploid strains are spheroplasted and fused, and diploid progeny regenerated and selected. By either method, diploid strains can be identified and selectively grown because, unlike their haploid parents, they do not have the same nutritional requirements. For example, the diploid cells may be grown in minimal medium. The diploid synthesis strategy has certain advantages. Diploid strains have the potential to produce enhanced levels of heterologous protein through broader complementation to underlying mutations, which may impact the production and/or secretion of recombinant protein.

As noted above, in some embodiments a haploid yeast may be transformed with a single or multiple vectors and mated or fused with a non-transformed cell to produce a diploid cell containing the vector or vectors. In other embodiments, a diploid yeast cell may be transformed with one or more vectors that provide for the expression and secretion of a desired heterologous polypeptide by the diploid yeast cell.

In one embodiment of the invention, two haploid strains are transformed with a library of polypeptides, e.g. a library of antibody heavy or light chains. Transformed haploid cells that synthesize the polypeptides are mated with the complementary haploid cells. The resulting diploid cells are screened for functional protein. The diploid cells provide a means of rapidly, conveniently and inexpensively bringing together a large number of combinations of polypeptides for functional testing. This technology is especially applicable for the generation of heterodimeric protein products, where optimized subunit synthesis levels are critical for functional protein expression and secretion.

In another embodiment of the invention, the expression level ratio of the two subunits is regulated in order to maximize product generation. Heterodimer subunit protein levels have been shown previously to impact the final product generation (Simmons L C, J Immunol Methods. 2002 May 1; 263(1-2):133-47). Regulation can be achieved prior to the mating step by selection for a marker present on the expression vector. By stably increasing the copy number of the vector, the expression level can be increased. In some cases, it may be desirable to increase the level of one chain relative to the other, so as to reach a balanced proportion between the subunits of the polypeptide. Antibiotic resistance markers are useful for this purpose, e.g. Zeocin resistance marker, G418 resistance, etc. and provide a means of enrichment for strains that contain multiple integrated copies of an expression vector in a strain by selecting for transformants that are resistant to higher levels of Zeocin or G418. The proper ratio, e.g. 1:1; 1:2; etc. of the subunit genes may be important for efficient protein production. Even when the same promoter is used to transcribe both subunits, many other factors contribute to the final level of protein expressed and therefore, it can be useful to increase the number of copies of one encoded gene relative to the other. Alternatively, diploid strains that produce higher levels of a polypeptide, relative to single copy vector strains, are created by mating two haploid strains, both of which have multiple copies of the expression vectors.

Host cells are transformed with the above-described expression vectors, mated to form diploid strains, and cultured in conventional nutrient media modified as appropriate for inducing promoters, selecting transformants or amplifying the genes encoding the desired sequences. A number of minimal media suitable for the growth of yeast are known in the art. Any of these media may be supplemented as necessary with salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Secreted proteins are recovered from the culture medium. A protease inhibitor, such as phenyl methyl sulfonyl fluoride (PMSF) may be useful to inhibit proteolytic degradation during purification, and antibiotics may be included to prevent the growth of adventitious contaminants. The composition may be concentrated, filtered, dialyzed, etc., using methods known in the art.

The diploid cells of the invention are grown for production purposes. Such production purposes desirably include growth in minimal media, which media lacks pre-formed amino acids and other complex biomolecules, e.g. media comprising ammonia as a nitrogen source, and glucose as an energy and carbon source, and salts as a source of phosphate, calcium and the like. Preferably such production media lacks selective agents such as antibiotics, amino acids, purines, pyrimidines, etc. The diploid cells can be grown to high cell density, for example at least about 50 g/L; more usually at least about 100 g/L; and may be at least about 300, about 400, about 500 g/L or more.

In one embodiment of the invention, the growth of the subject cells for production purposes is performed at low temperatures, which temperatures may be lowered during log phase, during stationary phase, or both. The term "low temperature" refers to temperatures of at least about 15° C., more usually at least about 17° C., and may be about 20° C., and is usually not more than about 25° C., more usually not more than about 22° C. Growth temperature can impact the production of full-length secreted proteins in production cultures, and decreasing the culture growth temperature can strongly enhances the intact product yield. The decreased temperature appears to assist intracellular trafficking through the folding and post-translational processing pathways used by the host to generate the target product, along with reduction of cellular protease degradation.

The methods of the invention provide for expression of secreted, active protein, preferably a mammalian protein. In the preferred particularly secreted, active antibodies, where "active antibodies", as used herein, refers to a correctly folded multimer of at least two properly paired chains, which accurately binds to its cognate antigen. Expression levels of active protein are usually at least about 10-50 mg/liter culture, more usually at least about 100 mg/liter, preferably at least about 500 mg/liter, and may be 1000 mg/liter or more.

The methods of the invention can provide for increased stability of the host and heterologous coding sequences during production. The stability is evidenced, for example, by maintenance of high levels of expression of time, where the starting level of expression is decreased by not more than about 20%, usually not more than 10%, and may be decreased by not more than about 5% over about 20 doublings, 50 doublings, 100 doublings, or more.

The strain stability also provides for maintenance of heterologous gene sequence integrity over time, where the sequence of the active coding sequence and requisite transcriptional regulatory elements are maintained in at least about 99% of the diploid cells, usually in at least about 99.9% of the diploid cells, and preferably in at least about 99.99% of the diploid cells over about 20 doublings, 50 doublings, 100 doublings, or more. Preferably, substantially all of the diploid cells maintain the sequence of the active coding sequence and requisite transcriptional regulatory elements.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

To demonstrate the efficacy of the diploid antibody production method the following reagents were prepared.

Antibody Genes:

Genes were cloned and constructed that directed the synthesis of three forms of a chimeric humanized mouse monoclonal antibody OKT3. The sources of the variable regions for use in these constructs can be found in Genbank. Accession number A22261; mouse OKT3 heavy chain (International Patent Application WO 9109967-A 3 11 Jul. 1991). Accession number A22259; mouse OKT3 light chain (International Patent Application WO 9109967-A 3 11 Jul. 1991).

All three forms utilized the identical $V_\kappa C_\kappa$ light chain gene (SEQ ID NO: 10). For the three heavy chain genes, all encoded the identical mouse variable region ($V_h$) but differed from each other in the amino acid sequence of the human heavy chain constant regions. The first construct directed the synthesis of a full-length wild-type heavy chain ($C_{\gamma 1}$) with its single normal N-linked glycosylation site present (full-length glycosylated heavy chain) (SEQ ID NO: 13 and No 14). The second gene directed the synthesis of a non-glycosylated heavy chain created by mutating a nucleotide in the sequence so that a threonine at position 301 was changed to an alanine in the glycosylation site recognition sequence (Asn-X-Thr/Ser) (full-length non-glycosylated heavy chain) (SEQ ID NO: 15). The third gene construct directed the synthesis of a heavy chain in which most of the constant region was deleted after the hinge region (Fab heavy chain) (SEQ ID NO: 16).

Expression Vector:

The vector contains the following functional components: 1) a mutant ColE1 origin of replication, which facilitates the replication of the plasmid vector in cells of the bacterium *Escherichia coli;* 2) a bacterial Sh ble gene, which confers resistance to the antibiotic Zeocin and serves as the selectable marker for transformations of both *E. coli* and *P. pastoris;* 3) an expression cassette composed of the glyceraldehyde dehydrogenase gene (GAP gene) promoter, fused to sequences encoding the *Saccharomyces cerevisiae* alpha mating factor pre pro secretion leader sequence, followed by sequences encoding a *P. pastoris* transcriptional termination signal from the *P. pastoris* alcohol oxidase I gene (AOX1). The Zeocin resistance marker gene provides a means of enrichment for strains that contain multiple integrated copies of an expression vector in a strain by selecting for transformants that are resistant to higher levels of Zeocin.

*P. pastoris* Strains:

The auxotrophic strains used for this example are the *P. pastoris* ade1 and ura3 strains, which require supplementation with adenine and uracil, respectively, for growth. Strains met1 and lys3 have also been used. Although any two complementing sets of auxotrophic strains could be used for the construction and maintenance of diploid strains, these two strains are especially suited for this method for two reasons. First, they grow more slowly than diploid strains that are the result of their mating or fusion. Thus, if a small number of haploid ade1 or ura3 cells remain present in a culture or arise through meiosis or other mechanism, the diploid strain should outgrow them in culture.

The second is that it is easy to monitor the sexual state of these strains since colonies of the diploid product of their mating are a normal white or cream color, whereas cells of any strains that are haploid ade1 mutants in a culture form a colony with distinct pink in color. In addition, any strains that are haploid ura3 mutants are resistant to the drug 5-fluoro-orotic acid (FOA) and can be sensitively identified by plating samples of a culture on minimal medium+uracil plates with FOA. On these plates, only uracil-requiring ura3 mutant (presumably haploid) strains can grow and form colonies. Thus, with haploid parent strains marked with ade1 and ura3, one can readily monitor the sexual state of the resulting antibody-producing diploid strains (haploid versus diploid).

Methods

Construction of pGAPZ-Alpha Expression Vectors for Transcription of Light and Heavy Chain Antibody Genes.

For cloning of both the light and heavy chain variable regions, cells of a mouse OKT3 CD3 hybridoma cell line were grown and total RNA extracted. Two RT-PCR reactions were then performed, one specific to light and one specific to heavy chain variable region encoding sequences of the OKT3 antibody genes. The primers employed to amplify out the heavy and light chain variable region were (SEQ ID NO:1) 5'-CCGCTCGAGAAAAGAGAGGCT-GAAGCTCAGGTCCAGCTGCAGCAGTC-3' and (SEQ ID NO:3) 5'-CCGCTCGAGAAAAGAGAGGCT-GAAGCTCAAATTGTTCTCACCCAGTCTCC-3' along with (SEQ ID NO:2) 5'-TGGGCCCTTGGTGGAGGCT-GAGGAGACTGTGAGAGTGGTGC-3' and (SEQ ID NO:4) 5'-GACAGATGGTGCAGCCACAGCCCGG TTT-ATTTCCAACTTTGTCC-3' for the respective variable regions.

For the human heavy and light chain constant region genes, a human leukocyte 5'-stretch plus cDNA library was purchased from Clontech (HL 5019t). Two PCR reactions were performed on this library using primers specific for the heavy and light chain constant regions, respectively (Heavy chain: (SEQ ID NO:6) 5'-GCACCACTCTCACAGTCTC-CTCAGCCTCCACCAAGGGCCCA-3 and (SEQ ID NO:5) 5'-ATAAGAATGCGGCCGCTCATTTACCCGGAGACA-GGGAG-3' for full length along with (SEQ ID NO:7) 5'-TGCGGCCGCTCATGGGCACGGTGGGCATGTGT-3' for FAB generation'; Light chain: (SEQ ID NO:9) 5'-GGA-CAAAGTTGGAAATAAACCGGGCTGTGGCTGCAC-CATCTGTC-3' and (SEQ ID NO:8) 5'-ATAAGAATGCG-GCCGCTAACACTCTCCCCTGTTGAAGCT-3'.

A DNA sequence encoding the mouse light chain variable region was fused in frame to a sequence encoding the human light chain constant region (SEQ ID NO: 11 and SEQ ID NO:12). A fragment encoding the final fusion construct was inserted into P. pastoris expression vector pGAPZ-alpha via ligation through 5'-XhoI and 3'-NotI sites in pGAPZ-alpha. DNA sequence encoding the mouse heavy variable region was fused in frame to sequences encoding each of the three human heavy chain constant regions. These fusion products were then inserted using a similar 5'-XhoI and 3'-NotI strategy into pGAPZ-alpha. (SEQ ID NO:13 and SEQ ID NO: 14 for the glycosylated version; SEQ ID NO: 15 for the aglycosylated version; SEQ ID NO: 16 for the Fab fragment). The proper antibody gene DNA sequences in all vectors were confirmed by direct DNA sequencing prior to further work.

Transformation of Expression Vectors into Haploid Ade1 Ura3, Met1 and Lys3 Host Strains of P. pastoris.

All methods used for transformation of haploid P. pastoris strains and genetic manipulation of the P. pastoris sexual cycle were as described in Higgins, D. R., and Cregg, J. M., Eds. 1998. *Pichia Protocols. Methods in Molecular Biology*. Humana Press, Totowa, N.J.

Prior to transformation, each expression vector was linearized within the GAP promoter sequences with AvrII to direct the integration of the vectors into the GAP promoter locus of the P. pastoris genome. Samples of each vector were then individually transformed into electrocompetent cultures of the ade1, ura3, met1 and lys3 strains by electroporation and successful transformants were selected on YPD Zeocin plates by their resistance to this antibiotic. Resulting colonies were selected, streaked for single colonies on YPD Zeocin plates and then examined for the presence of the antibody gene insert by a PCR assay on genomic DNA extracted from each strain for the proper antibody gene insert and/or by the ability of each strain to synthesize an antibody chain by a colony lift/immunoblot method (Wung et. al. Biotechniques 21 808-812 (1996). Haploid ade1, met1 and lys3 strains expressing one of the three heavy chain constructs were collected for diploid constructions along with haploid ura3 strain expressing light chain gene. The haploid expressing heavy chain genes were mated with the appropriate light chain haploid ura3 to generate diploid secreting protein.

Mating of Haploid Strains Synthesizing a Single Antibody Chain and Selection of Diploid Derivatives Synthesizing Tetrameric Functional Antibodies.

To mate P. pastoris haploid strains, each ade1 (or met1 or lys3) heavy chain producing strain to be crossed was streaked across a rich YPD plate and the ura3 light chain producing strain was streaked across a second YPD plate (~10 streaks per plate). After one or two days incubation at 30° C., cells from one plate containing heavy chain strains and one plate containing ura3 light chain strains were transferred to a sterile velvet cloth on a replica-plating block in a cross hatched pattern so that each heavy chain strain contained a patch of cells mixed with each light chain strain. The cross-streaked replica plated cells were then transferred to a mating plate and incubated at 25° C. to stimulate the initiation of mating between strains. After two days, the cells on the mating plates were transferred again to a sterile velvet on a replica-plating block and then transferred to minimal medium plates. These plates were incubated at 30° C. for three days to allow for the selective growth of colonies of prototrophic diploid strains. Colonies that arose were picked and streaked onto a second minimal medium plate to single colony isolate and purify each diploid strain. The resulting diploid cell lines were then examined for antibody production.

Putative diploid strains were tested to demonstrate that they were diploid and contained both expression vectors for antibody production. For diploidy, samples of a strain were spread on mating plates to stimulate them to go through meiosis and form spores. Haploid spore products were collected and tested for phenotype. If a significant percentage of the resulting spore products were single or double auxotrophs we concluded that the original strain must have been diploid. Diploid strains were examined for the presence of both antibody genes by extracting genomic DNA from each and utilizing this DNA in PCR reactions specific for each gene.

Fusion of Haploid Strains Synthesizing a Single Antibody Chain and Selection of Diploid Derivatives Synthesizing Tetrameric Functional Antibodies.

As an alternative to the mating procedure described above, individual cultures of single-chain antibody producing haploid ade1 and ura3 strains were spheroplasted and their resulting spheroplasts fused using polyethylene glycol/CaCl$_2$. The fused haploid strains were then embedded in agar containing 1 M sorbitol and minimal medium to allow diploid strains to regenerate their cell wall and grow into visible colonies. Resulting colonies were picked from the agar, streaked onto a minimal medium plate, and the plates incubated for two days at 30° C. to generate colonies from single cells of diploid cell lines. The resulting putative diploid cell lines were then examined for diploidy and antibody production as described above.

Purification and Analysis of Antibodies.

Figure 2:
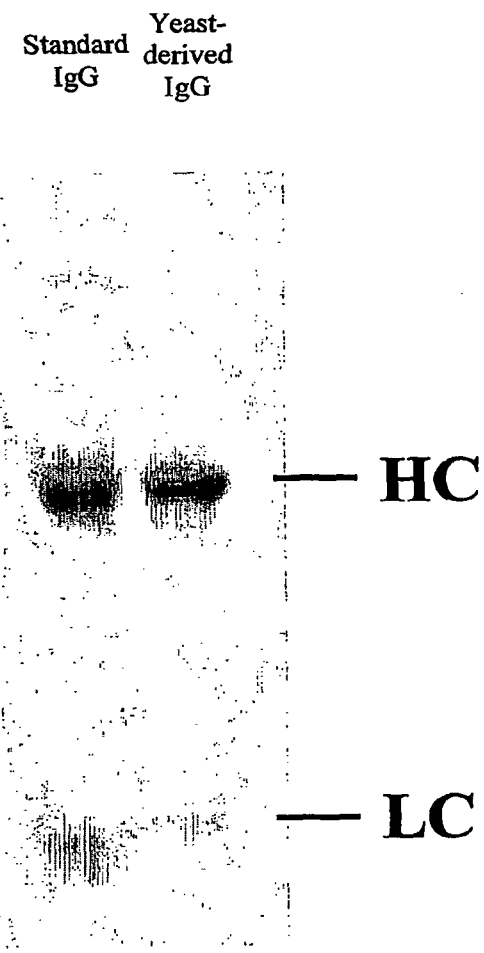
FIG. 2. Full length antibody production in *Pichia pastoris*. Heterologous expression of full-length antibody was conducted using a diploid *Pichia pastoris* strain. Exported antibody protein was isolated from conditioned media using Protein A affinity chromatography. An aliquot of the peak fraction is shown. The human IgG standard was derived from purified pooled human IgG.

A diploid strain for the production of full length antibody was derived through the mating of ura3 light chain strain 2252 and lys3 heavy chain strain 2254 using the methods described above. Culture media from shake-flask or fermenter cultures of diploid P. pastoris expression strains were collected and examined for the presence of antibody protein via SDS-PAGE and immunoblotting using antibodies directed against heavy and light chains of human IgG, or specifically against the heavy chain of IgG. The data is shown in FIG. 2.

Figure 3:
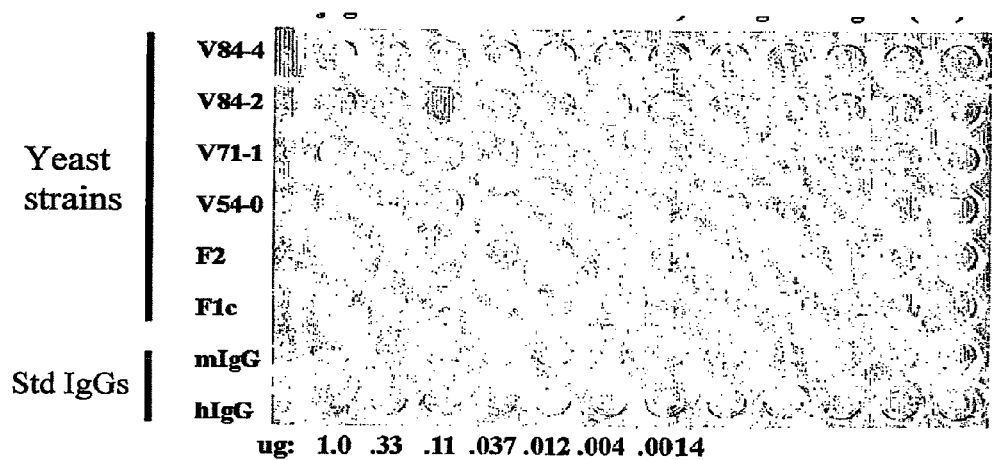
FIG. 3. Assembled antibody was detected and characterized from media supernatants from subclones of diploid *Pichia pastoris* strains, which were engineered to produce full-length mouse/human chimeric antibody. Microtiter plates were coated with Anti-human Fc selective antibodies to capture the antibody from the culture media. Correctly assembled antibody was detected through the use of a human selective (Fab')2, which recognized the paired heavy CH1 and κ light chain constant regions. Serial dilutions of clarified media were applied to the plate. Development was through standard ELISA visualization methods. The detection is selective as shown by the lack of any detectable signal in the mIgG standard.

To purify the yeast secreted antibodies, clarified media from antibody producing cultures were passed through a protein A column and after washing with 20 mM sodium phosphate, pH 7.0, binding buffer, protein A bound protein was eluted using 0.1 M glycine HCl buffer, pH 3.0. Fractions containing the most total protein were examined by Coomasie blue strained SDS-PAGE and immunoblotting for antibody protein. Fractions were also examined via an ELISA assay in which microtiter plates were first coated with F(ab')2 goat anti-human IgG, Fcγ (Jackson Immuno, Cat No. 109-006-008). Next plates were reacted with selected dilutions of yeast made antibodies. Finally, plates were reacted with HRP-conjugated goat anti-human F(ab')2 fragment of IgG F(ab')2 (Jackson Immuno, Cat No. 109-036-097). Plates were then developed with TMP substrate (Sigma Chemical) and reactions were quenched with 0.5 M HCl. Results were quantitated on a BioRad microtiter plate reader at 415 nm. The data is illustrated in FIG. 3.

Assay for Antibody Activity.

The recombinant yeast-derived chimeric antibody was evaluated for functional activity through immunohistochemical staining of cells containing the target antigen. The chimeric antibody selectively recognizes the CD3 complex found on T cells. Jurkat T cells were employed as a source of antigen and cell surface staining was conducted using procedures described in Andersson and Sander (Immunol Lett. 1989 Jan. 31; 20(2):115-20) or Andersson et. al. (Eur J Immunol. 1988 Dec.; 18(12):2081-4).

Figure 4:
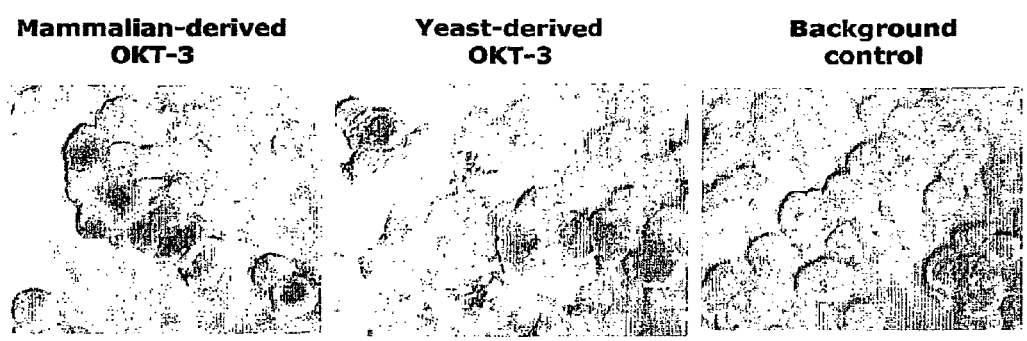
FIG. 4. *Pichia* generated recombinant antibody stains CD3 containing Jurkat T-cells as well as traditional mammalian-derived antibody. Jurkat T-cells were immobilized on glass slides and staining was conducted using the anti-CD3 antibody generated in yeast and mammalian cells. Detection was performed using a biotinylated-conjugated anti-rodent secondary antibody, and developed with an HRP-streptavidin derivative. The imagines are representative field of slide treated with each recombinant antibody. Background is control for development and conducted in the absence of the primary anti-CD3 antibody.

Jurkat T cells were immobilized on glass slides, blocked with the appropriate blocking serum and stained with mammalian and yeast generated recombinant primary antibody for 1 hour. The immobilized samples were then treated with peroxidase blocking agent followed by staining with a biotinylated Fc selective secondary antibody that is specific for each form of the antibody (anti-mouse for the mammalian and anti-human for the yeast). Detection was performed using a HRP-Streptavidin system. Digital imaging was performed to collect the data for each stained sample. Positive signal is detected in samples via a dark staining of the cells observed in the panels for mammalian-derived and yeast-derived OKT-3. This is data is shown in FIG. 4.

What is claimed is:

1. A diploid *Pichia pastoris* yeast culture which is cultured under conditions whereby the diploid *Pichia pastoris* yeast culture expresses and secretes into the culture medium a heterologous multichain polypeptide encoded by one or more heterologous DNAs operably linked to a promoter, wherein said one or more heterologous DNAs are expressed by diploid *Pichia pastoris* yeast cells comprised in said diploid *Pichia* yeast culture, wherein the heterologous multichain polypeptide is other than an antibody or antibody fragment that specifically binds to a target antigen, wherein the density of *Pichia pastoris* in the culture is at least 100 g/L.

2. The diploid *Pichia pastoris* yeast culture of claim 1 wherein the density of *Pichia pastoris* in the culture is at least 200 g/L.

3. The diploid *Pichia pastoris* yeast culture of claim 1 wherein the density of *Pichia pastoris* in the culture is at least 300 g/L.

4. The diploid *Pichia pastoris* yeast culture of claim 1 wherein the density of *Pichia pastoris* in the culture is at least 400 g/L.

5. The diploid *Pichia pastoris* yeast culture of claim 1 wherein the density of *Pichia pastoris* in the culture is at least 500 g/L.

6. The diploid *Pichia pastoris* yeast culture of claim 1 wherein said one or more heterologous DNAs are comprised on a plasmid.

7. The diploid *Pichia pastoris* yeast culture of claim 1 wherein said one or more heterologous DNAs are integrated into the chromosomal DNA of said yeast.

8. The diploid *Pichia pastoris* yeast culture of claim 1, wherein the heterologous polypeptide is selected from the group consisting of a hormone, growth factor, cytokine, lymphokine, enzyme, receptor, cytotoxin, lymphotoxin, immunotoxin, and a tumor polypeptide.

* * * * *

```
SEQUENCE LISTING

<160> NUMBER OF SEQ ID NOS: 9

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccgctcgaga aaagagaggc tgaagctcag gtccagctgc agcagtc              47

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgggcccttg gtggaggctg aggagactgt gagagtggtg c                    41

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccgctcgaga aaagagaggc tgaagctcaa attgttctca cccagtctcc           50

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 4
gacagatggt gcagccacag cccggttat ttccaactt gtcc                44

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ataagaatgc ggccgctcat ttacccggag acagggag                     38

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcaccactct cacagtctcc tcagcctcca ccaagggccc a                 41

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgcggccgct catgggcacg gtgggcatgt gt                           32

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ataagaatgc ggccgctaac actctcccct gttgaagct                    39

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggacaaagtt ggaaataaac cgggctgtgg ctgcaccatc tgtc              44
```